United States Patent [19]
Moulder et al.

[11] Patent Number: 6,037,768
[45] Date of Patent: Mar. 14, 2000

[54] PULSED EDDY CURRENT INSPECTIONS AND THE CALIBRATION AND DISPLAY OF INSPECTION RESULTS

[75] Inventors: John C. Moulder, West Des Moines, Iowa; Sunil K. Shaligram, Dallas, Tex.; Jay A. Bieber; James H. Rose, both of Ames, Iowa

[73] Assignee: Iowa State University Research Foundation, Inc., Ames, Iowa

[21] Appl. No.: 08/832,415

[22] Filed: Apr. 2, 1997

[51] Int. Cl.[7] ........................... G01R 33/12; G01N 27/82
[52] U.S. Cl. ...................... 324/225; 324/240; 324/242; 324/202
[58] Field of Search ........................ 324/225, 233, 324/234, 239, 240, 241, 242, 219, 220, 221, 202

[56] References Cited

U.S. PATENT DOCUMENTS

| | | |
|---|---|---|
| 2,985,824 | 5/1961 | Renken, Jr. . |
| 3,229,197 | 1/1966 | Renken, Jr. . |
| 3,361,960 | 1/1968 | Renken, Jr. et al. . |
| 3,526,829 | 9/1970 | Noble . |
| 3,848,182 | 11/1974 | Gerner et al. ........................ 324/233 |
| 4,414,508 | 11/1983 | Davis et al. . |
| 4,424,486 | 1/1984 | Denton et al. . |
| 4,495,466 | 1/1985 | Lakin . |
| 4,644,336 | 2/1987 | Mark, Jr. ........................... 324/220 |
| 4,843,319 | 6/1989 | Lara . |
| 4,843,320 | 6/1989 | Spies . |
| 5,006,800 | 4/1991 | Hedengren et al. . |
| 5,113,706 | 5/1992 | Pittaro . |
| 5,163,013 | 11/1992 | Herzer et al. . |
| 5,298,858 | 3/1994 | Harrison . |
| 5,406,500 | 4/1995 | Floret . |
| 5,510,709 | 4/1996 | Hurley et al. . |

FOREIGN PATENT DOCUMENTS

| | | |
|---|---|---|
| 1130870 | 10/1968 | United Kingdom . |
| 1481223 | 7/1977 | United Kingdom . |
| 2 086 057 | 5/1982 | United Kingdom . |
| WO 92/00520 | 1/1992 | WIPO . |

OTHER PUBLICATIONS

Moulder, et al., "Pulsed Eddy–Current Measurements of Corrosion–Induced Metal Loss: Theory and Experiment," *Review of Progress in Quantitative NDE*, vol. 14, pp. 2065–2072 (Plenum Press, NY, 1995, Thompson et al, eds.).

Harrison, "The Detection of Corrosion in Layered Structures Using Transient Eddy Currents," *Nondestructive Testing of Materials*, pp. 115–124 (IOS Press, 1995, R. Collins et al eds.).

Waidelich, "Pulsed Eddy Currents," *Research Techniques in Nondestructive Testing*, pp. 382–416, 1970.

(List continued on next page.)

*Primary Examiner*—Walter E. Snow
*Attorney, Agent, or Firm*—Fish & Richardson, P.C., P.A.

[57] ABSTRACT

A pulsed eddy current (PEC) instrument acquires PEC pulse responses from different locations on a structure being inspected. The difference between the acquired PEC pulse responses and a reference PEC response is determined to obtain time-domain difference signals having a time value and a magnitude value. The time and magnitude values are stored in memory with location information. An image display is provided that is determined from the stored magnitude values, although magnitude values for difference signals whose time values do not meet a defined time condition are filtered from the display. The time condition filters from the display known conditions such as the presence of fasteners, the presence of air-gaps between layers of the structure, and excessive PEC probe lift-off from the structure and filters the display so that only information from a particular layer or depth of the inspected structure is displayed. A quantified flaw measure can be determined by comparing the magnitude value to a calibration curve associated with a particular depth or layer of the structure. Also, Fourier transforms can be performed on the time-domain difference signal to obtain magnitude values at a multitude of frequencies which can be displayed in various formats, including an image display using a frequency condition for filtering.

48 Claims, 11 Drawing Sheets

OTHER PUBLICATIONS

Renkin, "A Pulsed Eddy Current Test System Using Reflected Fields," pp. 622–627, Dec. 1965.

Dodd, "A Portable Phase–Sensitive Eddy Current Instrument," *Material Evaluation,* pp. 33–36, Mar. 1968.

Lassahn, "A Comparison of Three Types of Eddy Current Systems," *Material Evaluation,* pp. 187–192, vol. 32, No. 9, Sep. 1974.

Hill et al., "Detecting Second–Layer Fatigue Cracks Under Installed Skins and Fasteners With Low–Frequency Eddy Current Array," *Materials Evaluation,* pp. 1398–1405, Dec. 1992.

Macecek, "Advanced Eddy Current Array Defect Imaging," *Review of Progress in Quantitative Nondestructive Evaluation,* pp. 995–1002, vol. 10A (Thompson & Chimenti, Plenum Press, NY, 1991, eds.).

Satveli, et al., "Impedance of a Coil Near an Imperfectly Layered Metal Structure: the Layer Approximation," pp. 2811–2821, *J. Appl. Phys.* 79(6), Mar. 15, 1996.

Mitra, et al., "Eddy–Current Measurements of Corrosion–Related Thinning in Aluminum Lap Splices," *Review of Progress in Quantitative Nondestructive Evaluation,* vol. 12, pp. 2003–2010 (Thompson & Chimenti, Plenum Press, NY, 1993).

Moulder, et al., "Characterizing the Performance of Eddy Current Probes Using Photoinductive Field–Mapping," *Res Nondestr Eval* (1992) 4:221–236.

Moulder, et al., "Thickness and Conductivity of Metallic Layers From Eddy Current Measurements," *Rev. Sci. Instrum.* pp. 3455–3465, 63(6), Jun. 1992.

Auld, et al., "Eddy–Current Signal Analysis and Inversion for Semielliptical Surface Cracks," *Journal of Nondestructive Evaluation,* pp. 79–94, vol. 7, Nos. 1/2, 1988.

*Cross-section*

*Raw data image*

*Time-gated image*

*Bottom layer*

PULSED EDDY CURRENT INSPECTIONS AND THE CALIBRATION AND DISPLAY OF INSPECTION RESULTS

STATEMENT AS TO FEDERALLY SPONSORED RESEARCH

This work was supported in part by Air Force Office of Scientific Research under AFOSR Grant No. F49620-93-1-0439DEF, and also in part by the Federal Aviation Administration under Grant Nos. 95-G-025 and 95-G-032.

FIELD OF THE INVENTION

The present invention relates to pulsed eddy current instruments for non-destructive inspections, and more particularly, to the display and calibration of inspection results.

BACKGROUND OF THE INVENTION

Non-destructive methods for characterizing damage caused by hidden corrosion and fatigue in layered structures such as aircraft lapjoints are a high priority for commercial airlines and the military. Eddy current instruments have long been used for non-destructive testing. Eddy currents penetrate into subsurface layers whether or not the layers are mechanically bonded, which is an advantage over ultrasonic techniques that require a mechanical bond between layers for the ultrasonic energy to penetrate to deeper layers.

Eddy current testing instruments include a probe that is positioned on the surface of a structure to be inspected. A coil in the probe is electrically excited, either by a sinusoidal or a pulsed signal, and a response is measured. Pulsed excitation causes the propagation of a highly attenuated traveling wave, which is governed by the diffusion equation, which states that the diffusive propagation of the eddy current pulse results in spatial broadening and a delay, or travel time, proportional to the square of the distance traveled.

Pulsed eddy current (PEC) methods have important advantages over sinusoidal methods. The pulsed eddy current method excites the probe with a step voltage function. The step function contains a continuum of frequencies. As a result, the response to several different frequencies can be measured with a single step. Because depth of penetration is dependent on the frequency of the excitation, information from a range of depths can be obtained with the one step function.

One PEC inspection instrument that has been developed employs pulsed eddy currents for characterizing corrosion-induced loss of metal in aircraft structures. See Moulder et al., "Pulsed eddy-current measurements of corrosion-induced metal loss:theory and experiment," *Review of Progress in Quantitative NDE,* Vol. 14, pp. 2065–2072 (Plenum Press, NY, 1995, Thompson et al. eds.). This instrument calculates and displays to the user a difference signal which is the difference between a time-domain PEC pulse response acquired by the PEC probe and a time-domain reference PEC pulse response. The user is able to see from the magnitude of the displayed difference signal whether there is metal loss associated with corrosion in the inspected sample structure. This instrument detects metal loss in all layers of a multi-layer structure.

Another PEC instrument is one that has been developed by the UK Defense Research Agency. See Harrison, "The detection of corrosion in layered structures using transient eddy currents," *Nondestructive Testing of Materials,* pp. 115–24 (IOS Press, 1995, R. Collins et al., eds.). This PEC instrument scans a probe across a layered structure and obtains time-domain magnetic-field transient responses. To obtain what is referred to as a "balanced transient," each of the responses is subtracted from a transient response obtained from an initial position. For each balanced transient, several amplitude time slices, ten in particular, are measured. The article cited above discloses that different timeslices may be displayed which gives information about different depths of the inspected structure. An amplitude window can also be set to obtain a color-coded display of only time-slice amplitudes within the set amplitude window.

SUMMARY OF THE INVENTION

The invention is a pulsed eddy current (PEC) instrument for inspecting a structure such as a layered structure of an aircraft. The instrument acquires PEC pulse responses from different locations on the structure being inspected. The difference between the acquired PEC pulse responses and a reference PEC response is determined to obtain difference signals having a time value and a magnitude value. The time and magnitude values are stored in memory with location information. An image display is provided that is determined from the magnitude values, although magnitude values for difference signals whose time values do not meet a defined time condition are filtered from the display.

The use of the defined time condition enables the filtering from the display of known conditions such as the presence of fasteners, excessive probe lift-off, and air gaps between layers, thereby allowing a user to detect more easily the existence of corrosion and other flaws where the known conditions exist. The use of the defined time condition also enables information from different depths of an inspected structure to be highlighted on the display. Because only a minimum number of significant characteristics (for example, one time measure indicative of depth, and one magnitude measure indicative of flaw severity) of the difference signal are used for each PEC pulse response, memory requirements, processing speeds, and display (and re-display) times are all minimized.

In different embodiments, the magnitude value can be a measure of peak amplitude, and the time value can be a measure of either, or a combined measure of, a time to the peak amplitude and/or a time to a zero-axis crossing after the peak amplitude. The time condition can be a time-gate having only a lower time limit, or having both a lower and an upper time limit. The time condition can be user selectable, or can be set automatically by the PEC instrument from, for example, geometric information about the structure under inspection. The time condition can also be determined from a user selection of a layer to be displayed. The reference PEC response signal can be ascertained experimentally from a known location, or theoretically from information about the geometry of the structure under inspection.

The PEC instrument can also determine a quantified measure of a detected flaw for a specified depth of the inspected structure. To do this, magnitude values, for difference signals having a time value that meets a time condition associated with the specified depth, are compared to a calibration curve of magnitude values versus quantified flaw measures. The quantified measure can be displayed in color-coded format according to the severity of the flaw. The calibration curve can be created experimentally by acquiring difference signal magnitude values from a number of locations having different known quantified flaw measures, and performing regression analysis on the magnitude values and flaw measures.

In another embodiment, Fourier transforms can be performed on the time-domain difference signal to obtain magnitude values at a multitude of frequencies. These magnitude values can be stored in memory with frequency and location information. After an image is displayed using the time-domain information, a plot of the stored magnitude values versus frequency for the difference signal acquired from a selected point can be displayed. This provides additional information to a user about the depth of a detected flaw, and in a frequency-domain format that is conventional for users of eddy current instruments. Also, the frequency-domain information can be used to create an image of the inspection results using a frequency condition to discriminate unwanted conditions and to focus on selected depths.

Other features and advantages of the invention will be apparent from the following detailed description, and from the claims.

DESCRIPTION OF THE PREFERRED EMBODIMENTS

Figure 1:
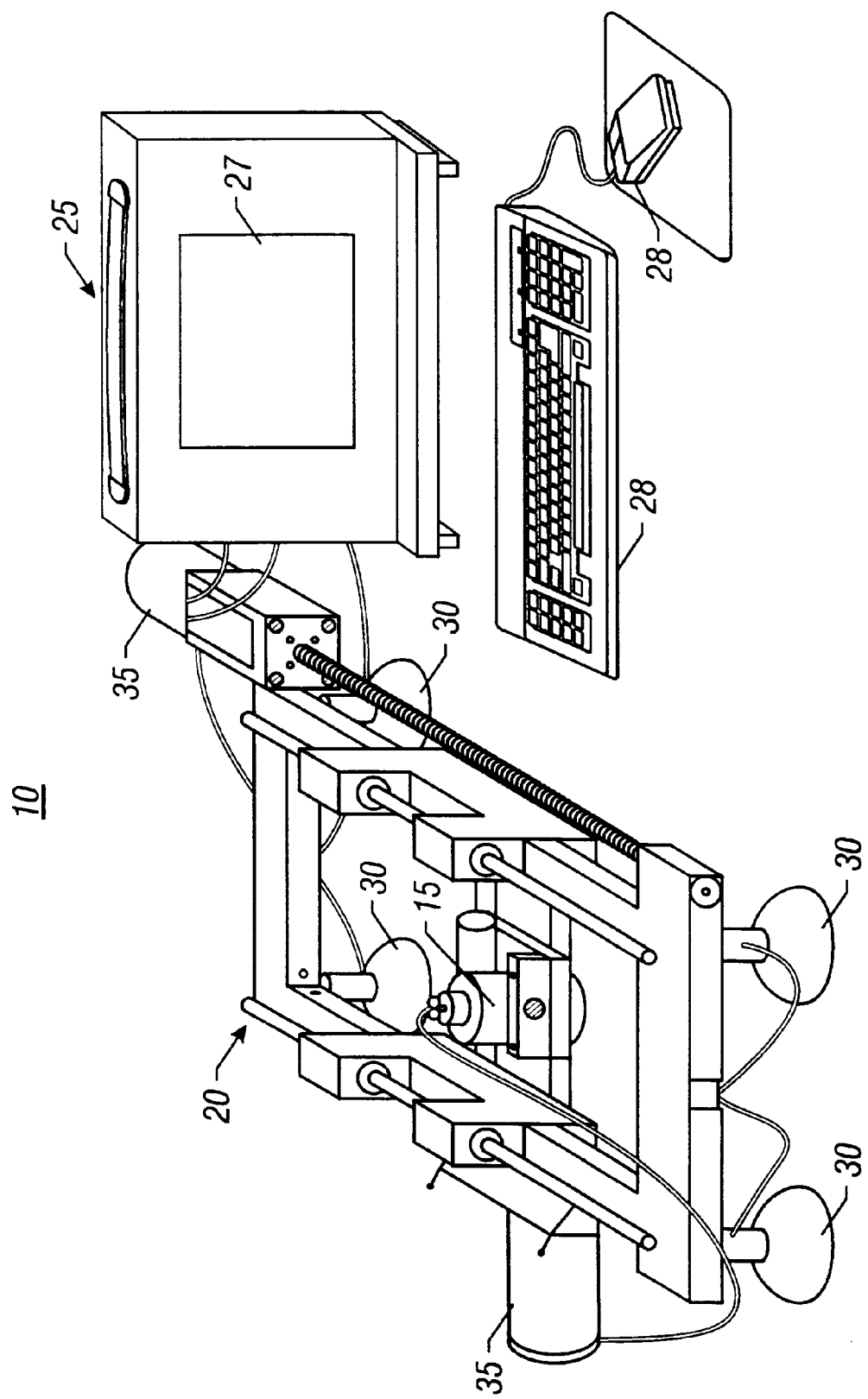
FIG. 1 is a pictorial drawing of a new PEC instrument.

FIG. 1 is pictorial diagram of a new pulsed (or transient) eddy current instrument 10. The instrument 10 includes a pulsed eddy current (PEC) probe 15, an x-y scanning apparatus 20 upon which the PEC probe 15 is mounted; and a rugged and portable customized computer 25 with a video display 27 and an input device 28 including a keyboard and mouse. The scanning apparatus 20 is driven by stepper motors 35. The scanning apparatus 20 also has four hydraulically actuable suction cup attachments 30 to enable the apparatus 20 to be mounted on a surface of a structure to be inspected, for example, on the underside of a fuselage of an aircraft.

Figure 2:
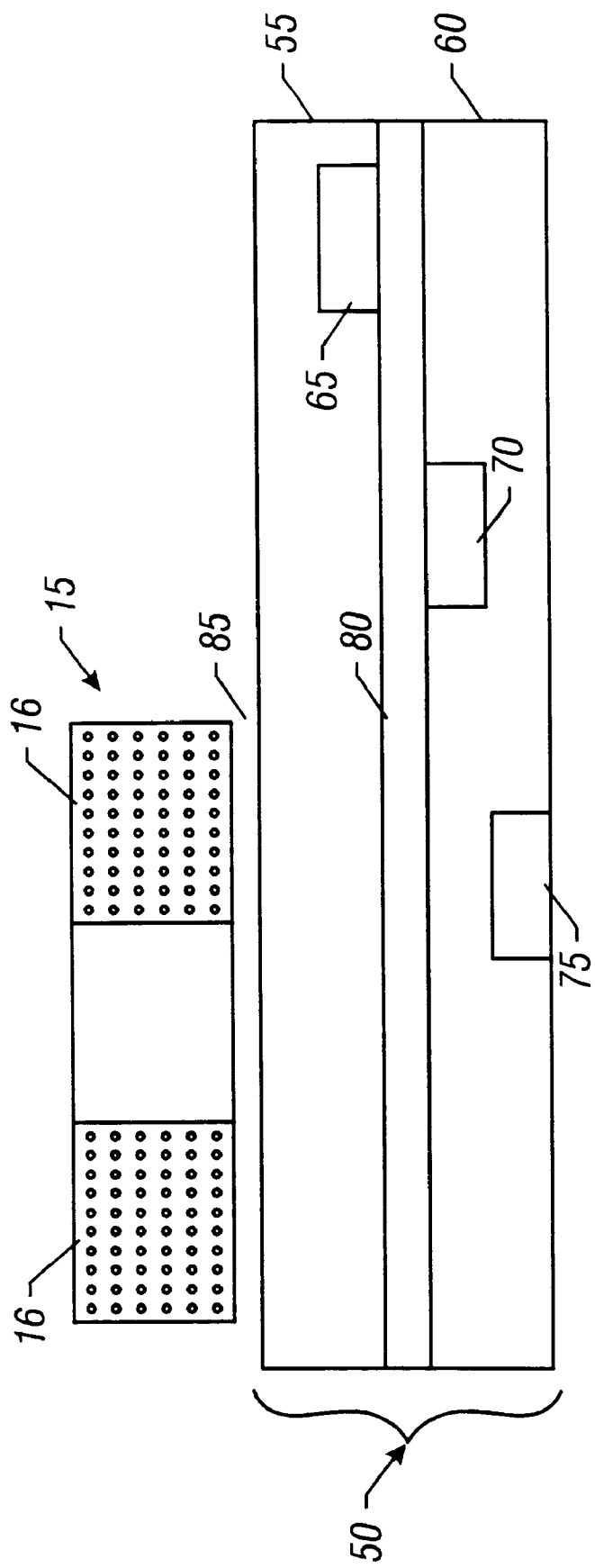
FIG. 2 is a cross-sectional diagram of a PEC probe and a sample structure to be inspected.

FIG. 2 shows a cross-section of a two-layer aircraft lapjoint 50 which is an example of a structure that can be inspected using the PEC instrument 10. The lapjoint 50 has a top layer 55 and a bottom layer 60, both of 2024 aluminum. There is typically some type of adhesive between the layers 55 and 60, and fasteners or rivets (not shown) are also used to secure the layers 55 and 60 together and to the aircraft. The lapjoint 50 is shown having areas of corrosion 65, 70 and 75 on the bottom of the top layer, top of the bottom layer, and bottom of the bottom layer, respectively.

The lapjoint 50 is shown also having an air gap 80 between the layers 55 and 60. An air gap 80 occurs often in aircraft, where physical distortion of the lapjoint 50 configuration is not uncommon. The existence of an air gap 80 is not an ideal condition, but it is not as problematic as a condition where corrosion exists between the layers 55 and 60. However, difficulty with prior eddy current inspections has been the occurrence of false positives from air gaps 80, which makes inspections of depths below the air gap 80 unreliable. Hence, it is desirable to be able to distinguish actual loss of metal from an air gap 80. In the past, this has been no trivial task.

FIG. 2 also shows the PEC probe 15 in cross-section, positioned as it would be during an inspection of the lapjoint 50. In this embodiment, the probe 15 includes a wire-wound, outer drive coil 16. In operation, excitation pulses are supplied to the drive coil 16. The response to the pulses measured by the probe 15, in this embodiment, is a time-domain voltage signal. That signal can be obtained either (1) from the outer drive coil 16, by measuring the voltage across a small (for example 1-ohm) current-sensing resistor in series with the outer coil 16 (in other words, an "absolute" probe 15 configuration); or (2) from a second inner pick-up coil (not shown) (a "pitch/catch" probe 15 configuration). Unless otherwise indicated, the PEC response signals discussed herein have been obtained by a probe 15 having the "absolute" configuration.

Another air gap 85, this one between the probe 15 and the lapjoint 50, is known as "lift-off." The probe 15 has a constant built-in wear surface, which provides a lift-off of approximately 0.007 of an inch. Ideally, lift-off remains constant at 0.007 of an inch during a scan; however, due to possible irregularities in a lapjoint 50 surface (due to fasteners, dents, or paint thickness variations, for example), greater lift-off may occasionally occur and pose a possibility of obtaining anomalous inspection results.

Overview of the Inspection Method

Before an inspection, the PEC instrument 10 is calibrated, either experimentally or theoretically, with a reference PEC response signal of a structure for the structure type to be inspected. After being calibrated, the PEC instrument 10 is used to perform an inspection of a structure. With the scanning apparatus 20 mounted on the surface of the structure to be inspected, a user interacts with the computer 25 to select an area to be inspected and also to initiate a scan of that area. The PEC probe 15, under computer and motor-driven control, is scanned in serpentine fashion over the selected surface area. During the scan the PEC probe 15 is energized with periodic pulses and the resulting PEC response signals are measured. The measured PEC response signals for each location of the scan are processed by the computer 25, and processed results are stored in the memory of the computer 25.

After the scan is complete, the user interacts with the computer 25 to obtain an image display showing the location and severity of flaws (for example, corrosion and cracks) in the structure. The display is provided on the PC's video display 27. Using discrimination techniques in accordance with the invention, the user is able to filter unwanted information. For example, the user is able to display only a selected depth range of the scanned structure, and is also able to filter from the display known conditions such as the existence of fasteners and air gaps, and also excessive probe lift-off. This provides a display that shows more clearly any flaws in the inspected structure.

Details of the PEC Instrument and the Inspection Method

Now for a more detailed description of the PEC instrument 10, reference will be made to FIG. 3 which shows the PEC instrument 10 in block diagram format. The computer 25 includes a rugged off-the-shelf portable personal computer (PC) 100 with three ISA expansion cards 120, 140 and 160. The first card 120 has a pulse generator 122 for supplying the periodic excitation pulses to the PEC probe 15. The pulse generator 122 is controlled by a microcontroller 124, which is also part of the custom card 120 and which has a built-in pulse width modulator.

Figure 4A:
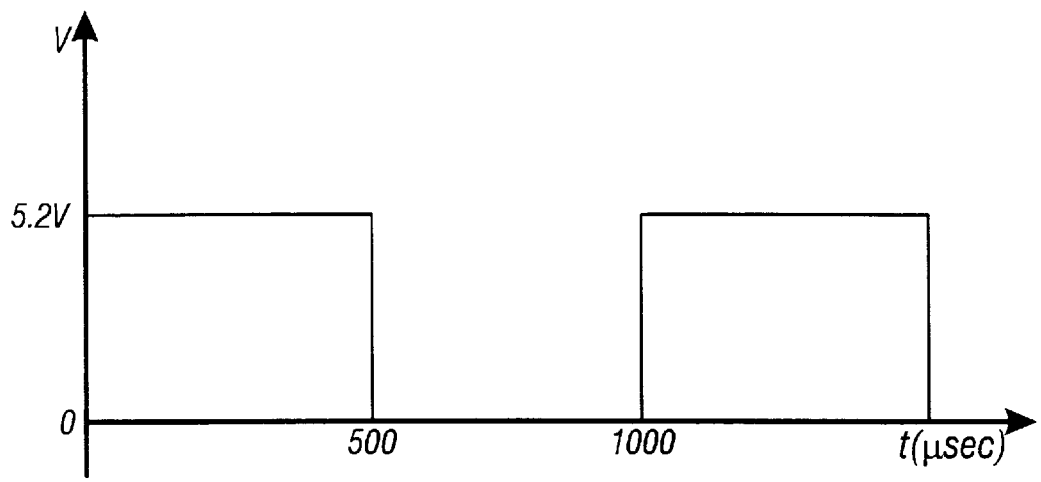
FIGS. 4A–B are timing diagrams of excitation pulses and PEC response signals.

FIG. 4A shows an example periodic excitation pulse train. The frequency, duty cycle, and amplitude of the pulse train are all selectable by the user. In this embodiment, the user is able to select a frequency in a range from 70 Hz to 1 MHz, an amplitude in a range from zero to ten volts, and a duty cycle in a range from 0 to 100%. For the pulse train shown in FIG. 4A, the selected frequency is 1 kHz, the selected duty cycle is 50%, and the selected amplitude is 5.2 volts. Different values are selected depending on the structure being inspected and the type of inspection desired. For example, for deeper inspections, the user may need to use higher amplitude pulses and lower frequencies. Also, different frequency, amplitude and duty cycles may be needed for different types of probes 15.

As discussed above, in the "absolute" mode of operation, the coil current resulting in the probe 15 during each pulse is detected by sensing the voltage drop across a 1-ohm resistor in series with the coil of the probe 15. The sensed signal is conditioned by circuitry 126 and forwarded to a data acquisition card 140. The data acquisition card 140 is a 16-bit, 1 MHz sampling-rate, analog-to-digital board which may be obtained, for example, from Analogic Corporation. For the frequency, amplitude, and duty cycle settings shown in FIG. 4A, a total of 512 (that is, $2^9$) samples are acquired for each pulse response, and those samples values are stored in temporary memory 144. When all of the 512 samples are acquired, the data acquisition card 140 immediately forwards the digitized time-domain PEC response signal via an ISA bus 180 to the PC 100 for processing. Other numbers of total samples can be acquired alternatively.

Meanwhile, the position of the probe 15 is controlled and monitored by a motor controller card 160 for the scanner's stepper motors 35. The motor controller card 160 can be, for example, an AT6400 motor controller card manufactured by Compumotor Controls. For each digitized PEC response signal that is acquired, the location information associated therewith is ascertained and associated with the digitized PEC response signal acquired from that location.

Processing Acquired PEC Response Signals

Figure 4B:
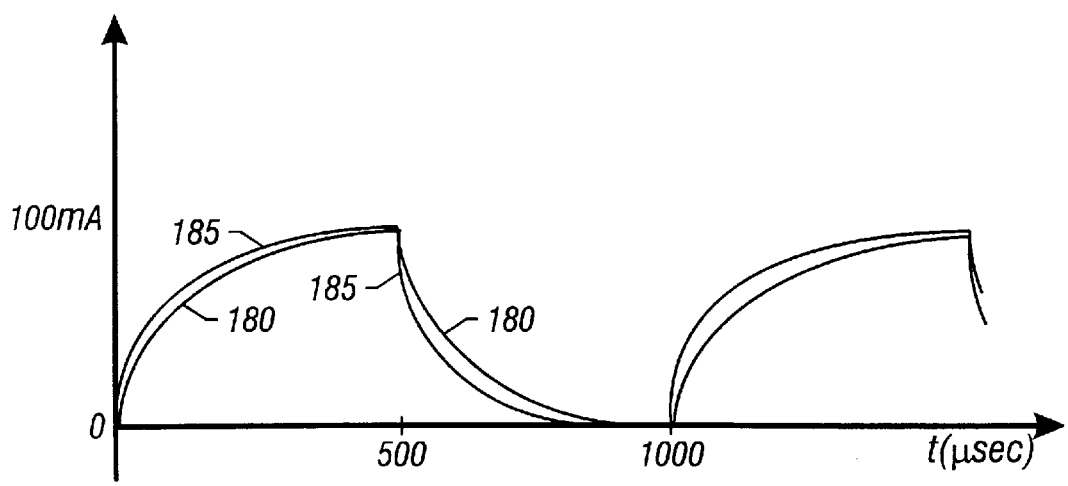

The processing of each acquired PEC response signal is executed by software (as described functionally herein) residing in the PC 100. The software can be implemented in a variety of ways known to those of skill in the art. The processing is performed as each digitized PEC response signal is received from the data acquisition card 140. The first step of the processing is to determine the difference between the time-domain reference PEC response signal, also digitized, and the acquired digitized PEC response signal. To obtain a positive difference signal, it may be that the reference PEC response signal is subtracted from the acquired PEC response signal or vice-versa, depending on which of the two signals are expected to have a greater magnitude in flaw areas. FIG. 4B shows a typical reference PEC response signal 180 plotted for comparison with a PEC response signal 185 acquired from a flaw area.

As discussed above, the reference PEC response signal is ascertained prior to an inspection scan. In the present embodiment, this is done by obtaining a PEC response signal from a structure of the type under inspection. The reference structure can be a calibration sample, or a portion of the structure to be inspected. The reference structure (or location) is one that the user knows to be flaw-free. In some cases, the reference structure may have some other known characteristic, for example, the thickest part of the sample. Instead of acquiring this reference PEC response signal experimentally every time a different structure type needs to be inspected, a database of reference PEC response signals for a number of different structure types can be created and stored in a non-volatile memory 104 of the PC 100. With this approach, the user selects, with the input device 28, the structure type to be inspected, which loads the respective digitized reference PEC response signal into a RAM 102. It may be necessary, however, to account for any difference between the temperature at which the reference PEC response signals in the database were taken and the temperature of the structure to be inspected.

The reference PEC response signal could also be calculated theoretically from known parameters for the probe 16 and the structure to be inspected. Coil parameters needed to make the calculation include number of turns, height, inner diameter, outer diameter, resistance, and lift-off distance. The structure parameters include conductivity and permeability, thickness and the geometry (e.g., number and thickness of layers). Because a PEC pulse response is also affected by temperature, the temperature at which the inspection is to be conducted can also be entered by a user and employed in the theoretical calculation of the reference PEC response signal.

To acquire a reference PEC response signal experimentally, the user selects, with the mouse 29, a reference location, whereupon the scanning apparatus 20 moves the probe 15 to that location. With the probe 15 properly positioned, the user enters, at the input device 28, a command that causes the reference PEC response signal to be acquired. The reference PEC signal is digitized and stored in RAM 102 of PC 100.

Figure 5:
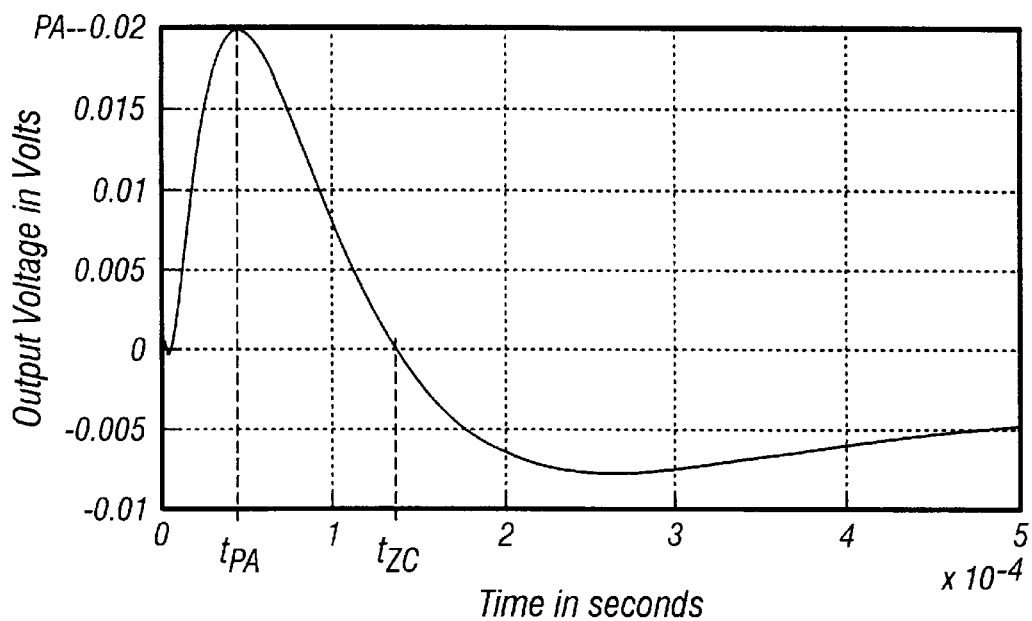
FIG. 5 is a timing diagram of a difference signal.

The subtraction operation (that is, the subtraction of the acquired PEC response signal from the reference PEC response signal or vice-versa) yields a digitized time-domain difference signal. FIG. 5 shows a typical difference signal from an aircraft lapjoint (see FIG. 2) containing an artificially thinned region (which simulates the existence of corrosion). The time-domain difference signal has a peak amplitude (PA), a time to peak amplitude ($t_{PA}$), and a zero-axis crossing time ($t_{ZC}$).

Information Conveyed by the Difference Signal

Theoretical calculations and experiments conducted by the Center for Nondestructive Evaluation and the FAA Center for Aviation Systems Reliability at Iowa State University yielded insight into the nature and information conveyed in the difference signal. FIGS. 6A–D illustrate some of the results of the theoretical calculations and experiments. These results are also published at Moulder et al., "Pulsed eddy-current measurements of corrosion-induced metal loss: theory and experiment," *Review of Progress in Quantitative NDE*, vol. 14, pp. 2065–2072 (Plenum Press, NY, 1995, Thompson et al. eds.).

Figure 6A:
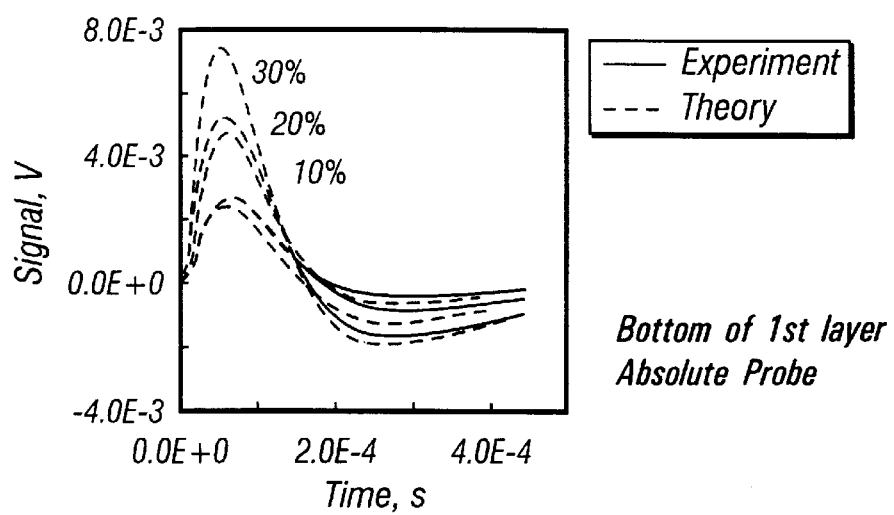
FIGS. 6A–C are timing diagrams of various difference signals.
Figure 6B:
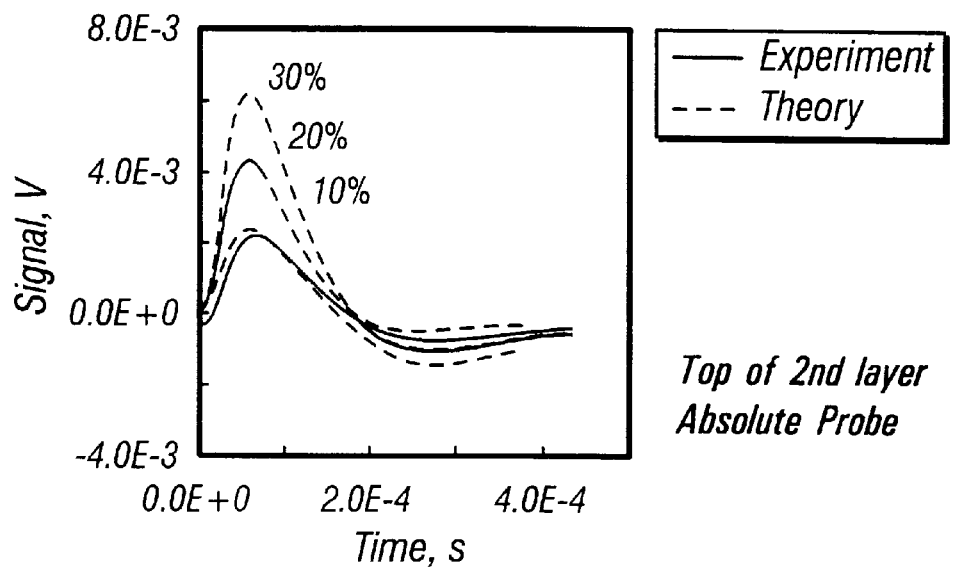

FIG. 6A shows time-domain difference signals, derived both theoretically and experimentally, for aircraft lapjoints 50 (see FIG. 2) having 10, 20, and 30% thinning of the aluminum at the bottom 65 of the top layer 55. The percent measures are a percentage of the total thickness of the respective layer. When the thinning is located at the top 70 of the bottom layer 60, a similar set of time-domain difference signals is obtained, as shown in FIG. 6B, albeit with generally lower peak amplitudes and longer zero-axis crossing times.

Figure 6C:
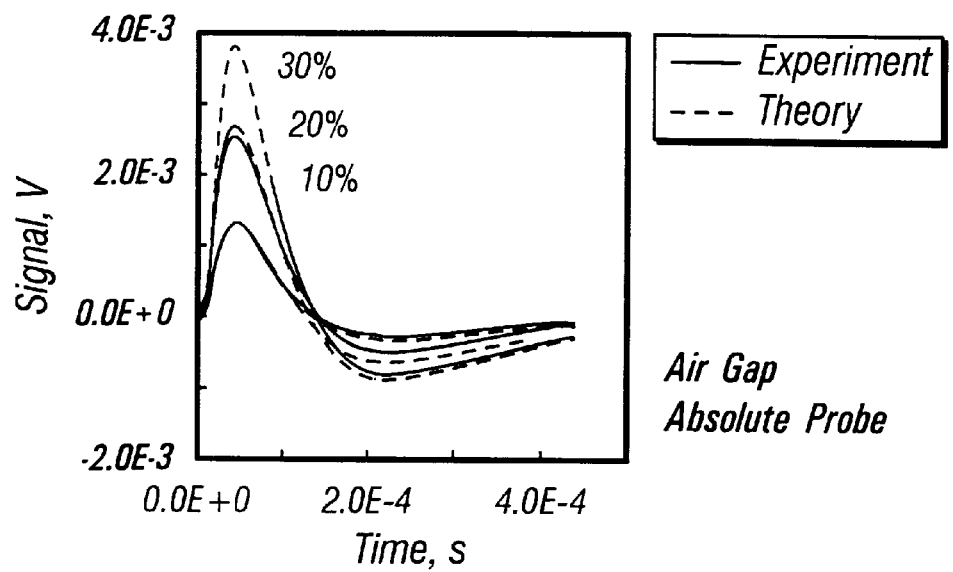

FIG. 6C shows time-domain difference signals where there was no change in thickness of metal in the layers 55 and 60, but where the two layers 55 and 60 were separated by increasing numbers of non-conductive spacers. The percent measure here is for the thickness of the air gap 80 as a percentage of the thickness of one of the layers, 55 or 60. Although the difference signals acquired from areas of air gaps 80 are comparable in magnitude to the signals from metal loss, they have much shorter zero-axis crossing times. This is believed to be because the total thickness of metal below the coil remains constant, which results in a lower inductance, and hence faster rise and decay times for the probe 15 coil than occurs when there is metal loss under the probe 15 coil.

Figure 6D:
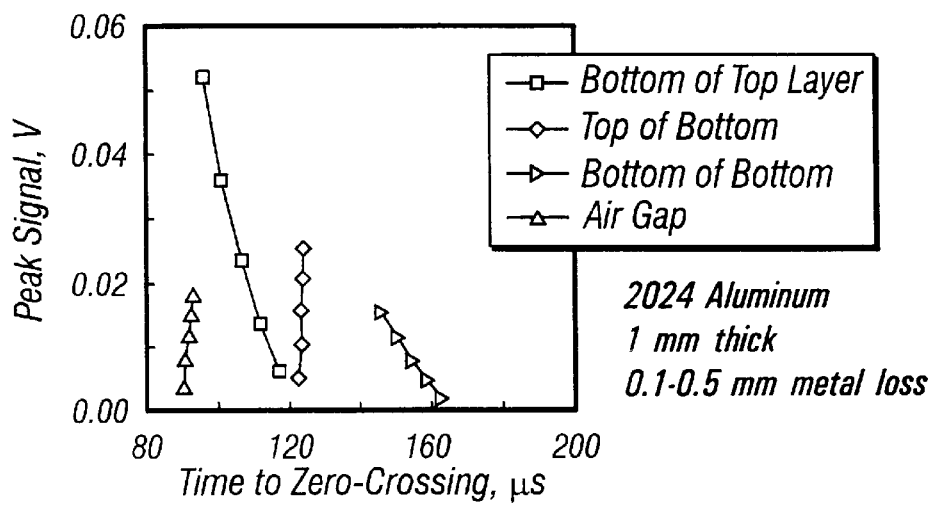
FIG. 6D is a plot of peak amplitudes versus zero-axis crossing times for the difference signals of FIGS. 6A–C.

FIG. 6D graphically illustrates the peak amplitude of the difference signals versus the time at which the signal crosses zero. As was recognized in Moulder et al., "Pulsed eddy-current measurements" (supra), difference signals from locations with metal loss occurring in the top layer 55 have the largest peak amplitude, since they suffer the least attenuation by passing through the metal. Also, the zero-axis-crossing times separate the signals into four different classes. Loss of metal at the deepest position shown (bottom of the bottom layer) leads to the longest time to cross zero, while the separation of the layers 55 and 60 with no loss of metal leads to the shortest time to cross zero.

Figure 7:
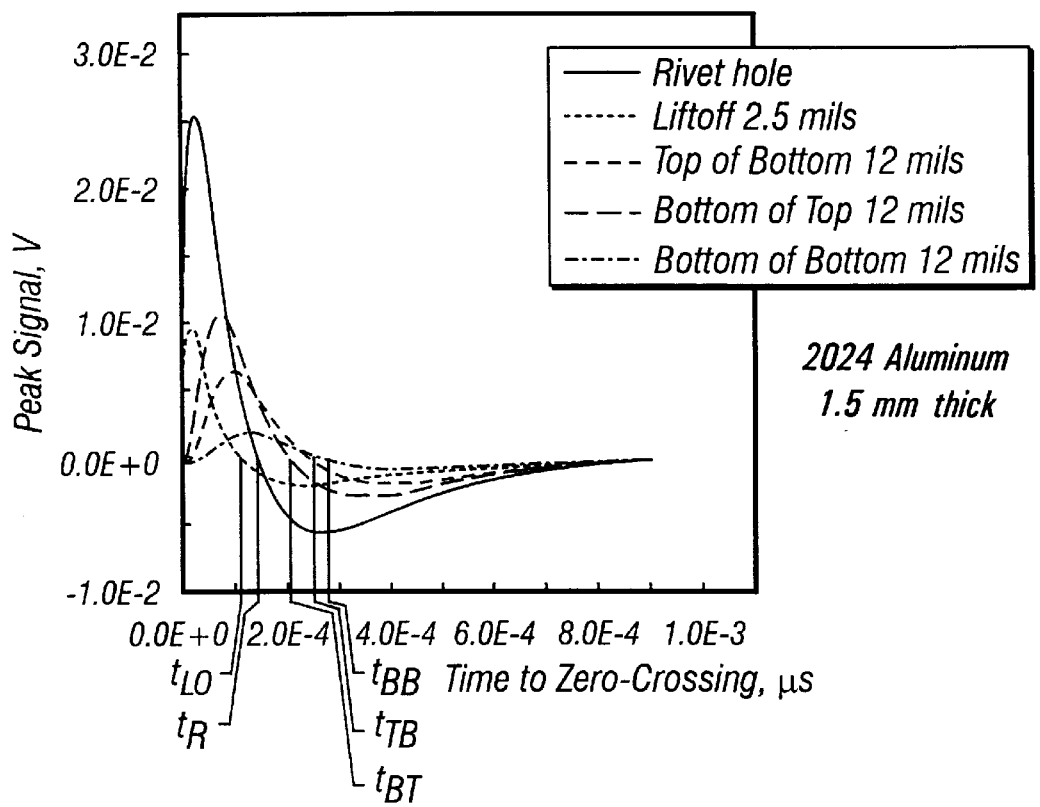
FIG. 7 is a timing diagram of various difference signals.

Subsequently conducted experiments, which were not published at Moulder et al., "Pulsed eddy-current instruments" (supra), produced information about difference signals for two additional conditions: (1) those acquired from fastener or rivet locations; and (2) those acquired where there was lift-off of the probe 15 of $2.5 \times 10^{-3}$ inch. The difference signals that were found for these conditions are shown in FIG. 7, with the zero-axis crossing time for lift-off designated $t_{LO}$ and that for the rivet hole, $t_R$. FIG. 7 also shows, for comparison, difference signals acquired where there was metal thinning of $12 \times 10^{-3}$ inch (that is, 20% thinning) on the bottom of the top layer, top of the bottom layer, and bottom of the bottom layer, whose zero-axis crossing times are indicated as $t_{BT}$, $t_{TB}$ and $t_{BB}$, respectively. Now it is seen that the zero-axis crossing times for the difference signals acquired both from fastener locations and with excess lift-off (as well as from air gap 80 locations as shown in FIG. 6D) are all earlier than the zero-axis crossing times for corrosion locations no matter the depth of the corrosion. The same is true for the peak amplitude times.

Further, a frequency-domain spectrum of magnitude values can be mathematically derived by means of a discrete Fourier transform of the time-domain difference signal. The result will be a magnitude measure at different frequencies of a spectrum of frequencies. The frequency corresponds to the depth of what has been detected, with lower frequencies corresponding to deeper depths.

Display of Inspection Results

Figure 3:
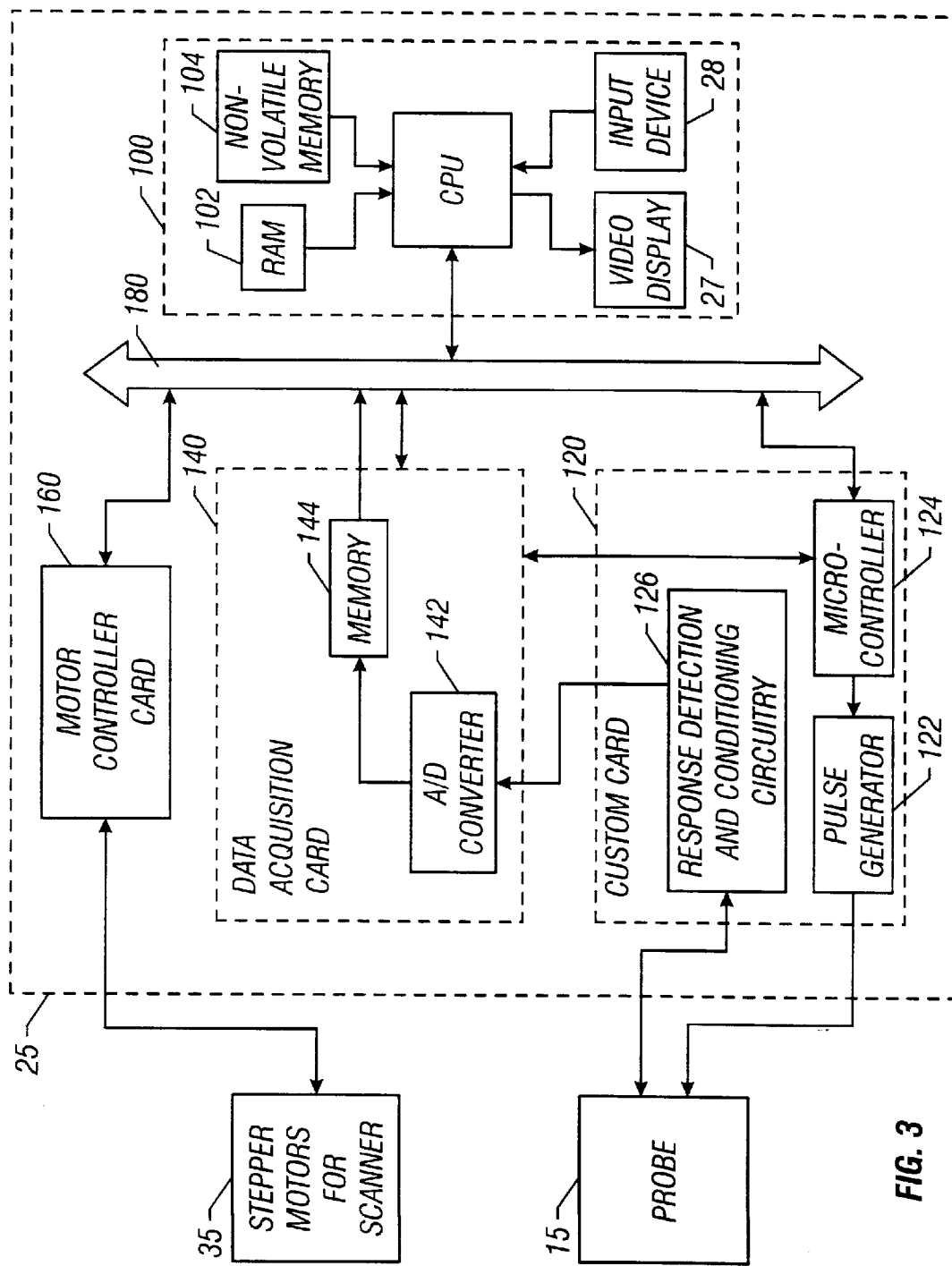
FIG. 3 is a block diagram of the PEC instrument of FIG. 1.

As a difference signal is found by the above-described subtraction operation, the peak amplitude and zero-axis time are determined and stored along with the x-y coordinates in an image file in non-volatile memory 104 (see FIG. 3). Once all of the scanned raw image data have been acquired, the user can obtain a variety of C-scan image displays of the inspection results. With the input device 28, the user selects parameters for the display, including a peak amplitude range and a time-gate. The peak amplitude range includes maximum and minimum expected peak amplitudes, $PA_{MAX}$ and $PA_{MIN}$ for the acquired difference signals. The peak amplitude of each of the difference signals is assigned an index value corresponding to one of a spectrum of colors. Peak amplitudes are assigned colors from a multi-color look-up table. The equation for the color index value is as follows:

$$\text{Index } (x, y) = \frac{n * (PA - PA_{\text{MIN}})}{PA_{\text{MAX}} - PA_{\text{MIN}}}$$

where n is the number of index values which in this case is 10, PA is the peak amplitude of the acquired difference signal, and $PA_{MAX}$ and $PA_{MIN}$ are as defined above.

Figure 8:
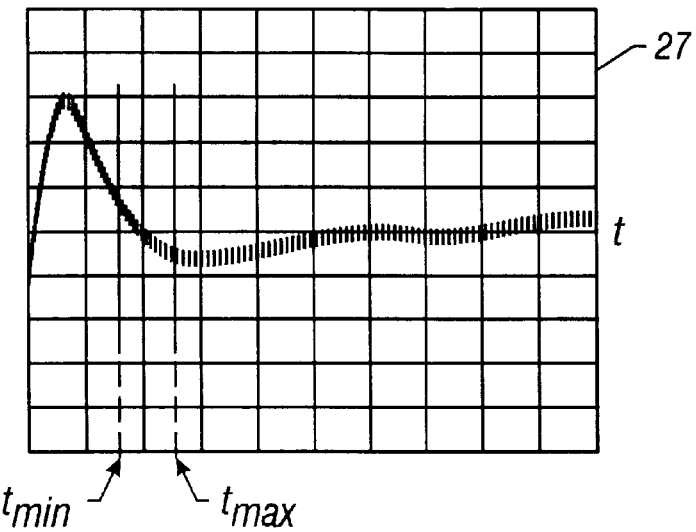
FIG. 8 is a video display of a difference signal, with an illustration of a time-gate thereon.

The time-gate is selected by selecting a minimum and a maximum zero-axis crossing time, $t_{min}$ to $t_{max}$, as shown in FIG. 8. Each difference signal whose zero-axis crossing time $t_{ZC}$ does not lie within the selected time-gate is assigned an index value which corresponds to no corrosion, whereas signals that lie within the time-gate are assigned an index value prescribed by their peak amplitudes and the index-value equation stated above. Hence, the following equation results:

$$\text{Index}(x, y) = \begin{cases} \left[\frac{n * (PA - PA_{\min})}{(PA_{\max} - PA_{\min})}\right] & \text{if } (t_{\min} < t_{ZC} < t_{\max}) \text{ and } (PA_{\max} < PA < PA_{\min}) \\ n & \text{if } PA \geq PA_{\max} \\ 0 & \text{if } (PA \leq PA_{\min}) \text{ or } (t_{ZC} < t_{\min}) \text{ or } (t_{ZC} > t_{\max}) \end{cases}$$

This final equation represents the manner by which an image of the inspection results is displayed. After an initial C-scan image is displayed, the user can later select a different amplitude range and/or time-gate and have a different C-scan image displayed, because the raw difference signal information remains stored in the non-volatile memory 104 (see FIG. 3).

Figure 9A:
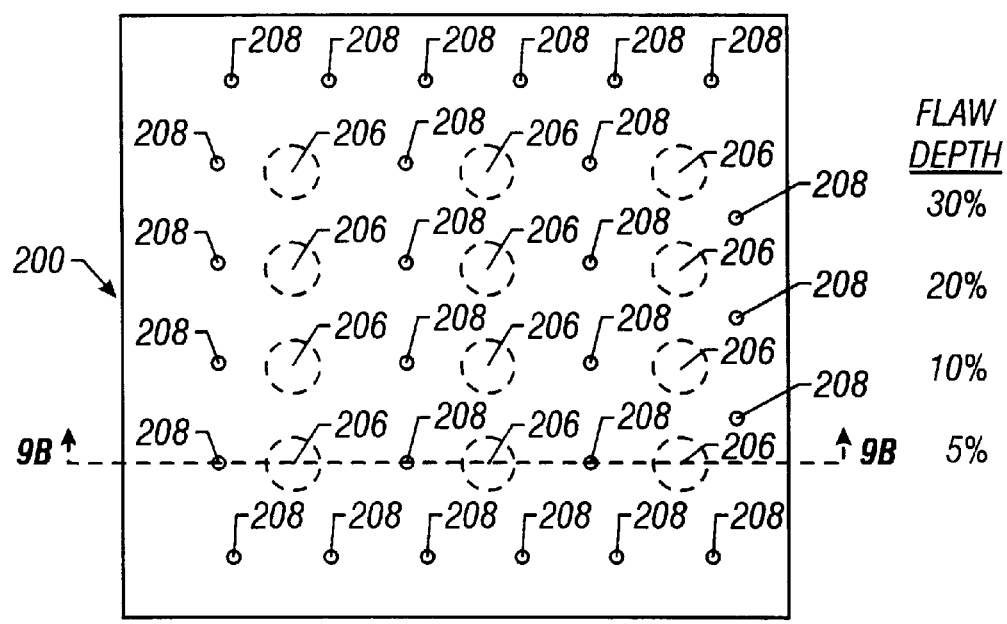
FIG. 9A is a top plan view, and FIG. 9B a cross-sectional view, of a structure to be inspected.
Figure 9B:
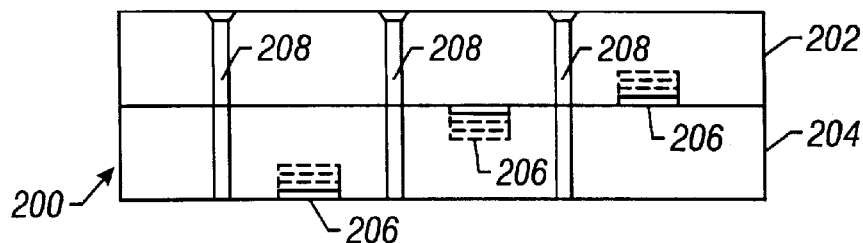

To demonstrate the PEC instrument's display capabilities, an inspection was performed on a lapjoint calibration sample 200 comprising two plates of 0.062-inch 2024 aluminum 202 and 204, as shown in FIGS. 9A–B. Flat bottom holes 206, 0.75 inch in diameter, were machined into the surface of each layer, with depths of 5, 10, 20, and 30%. (Each horizontal row of holes 206 shown in FIG. 9A is of the same percent depth as indicated at the right of the Figure, but the holes 206 in each horizontal row are in different layers, 202 or 204, of the sample 200.) Holes 208 were also drilled in the sample to simulate rivets on 1-inch centers.

Figure 10A:
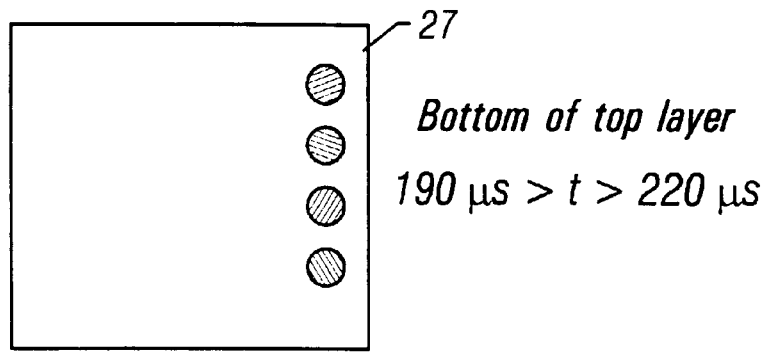
FIGS. 10A–C are illustrations of video displays of the results of an inspection of the structure of FIG. 9, with different time-gates selected.
Figure 10B:
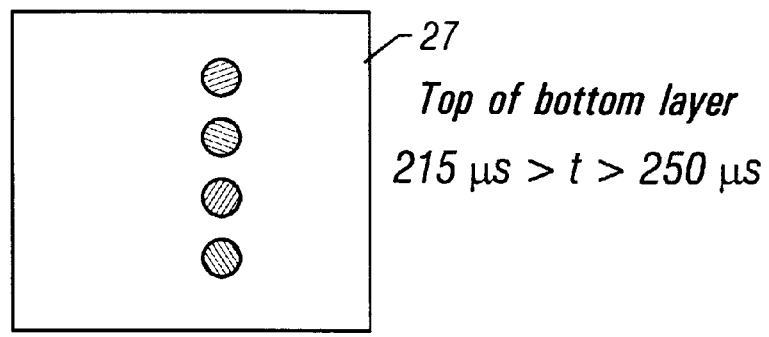
Figure 10C:
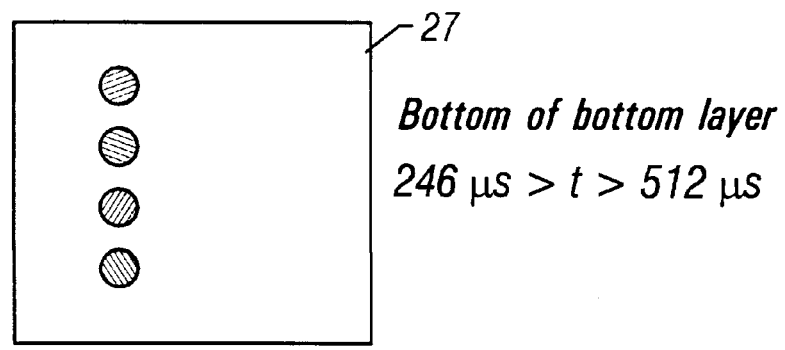

FIGS. 10A–C show illustrations of three different image visual displays obtained when different time-gates are selected. FIG. 10A is with a time-gate of 190 µs to 220 µs; therefore, only metal thinning at the bottom of the top layer is shown. FIG. 10B is with a time-gate set to 215 µs to 250 µs, so only metal thinning at the top of the bottom layer is shown. Finally, FIG. 10C is with a time-gate set to 246 µs to 512 µs, so only metal thinning at the bottom of the bottom layer is shown.

In addition to showing only the corrosion only at a selected depth range, setting a particular time-gate has the additional effect of filtering PEC response signals acquired from fasteners and air gap 80 locations, or acquired with an unintended increase in lift-off. As will be recalled, these conditions yield difference signals with zero-axis crossing times that are sooner than the zero-axis crossing times for corrosion existing in either of the two layers 55 and 60. Therefore, the three time-gated visual displays of FIGS. 10A–C show minimal interference from the simulated rivets 208. As such, where there was corrosion in the vicinity of a fastener, that corrosion was easier to detect on the display.

Figure 11A:
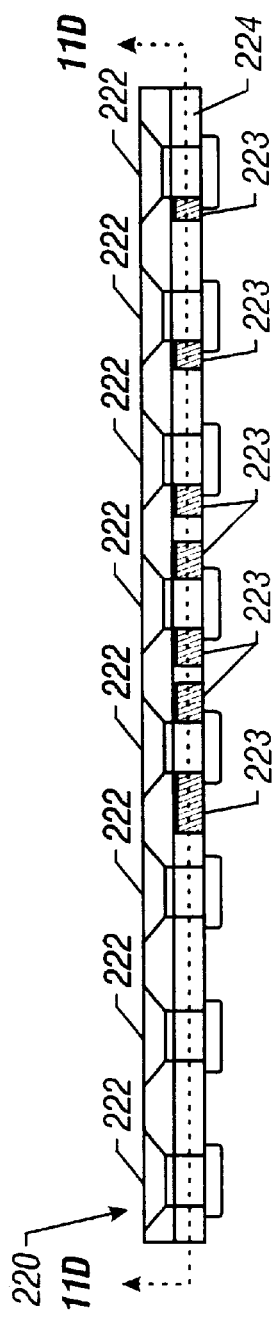
FIG. 11A is a cross-sectional view, and FIG. 11D a top plan view, of a structure for inspection.
Figure 11B:
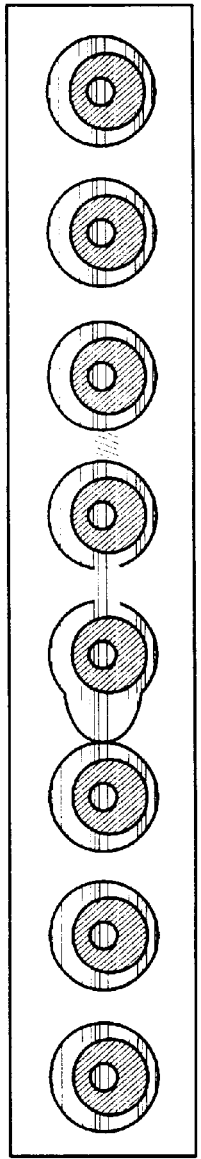
FIG. 11B is an illustration of a video display of the results of an inspection of the structure of FIGS. 11A and 11D without time-gating.
Figure 11C:
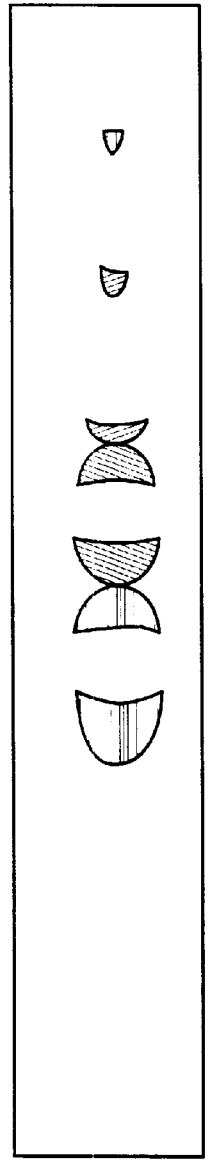
FIG. 11C is an illustration of a display of the same inspection results with time-gating.
Figure 11D:
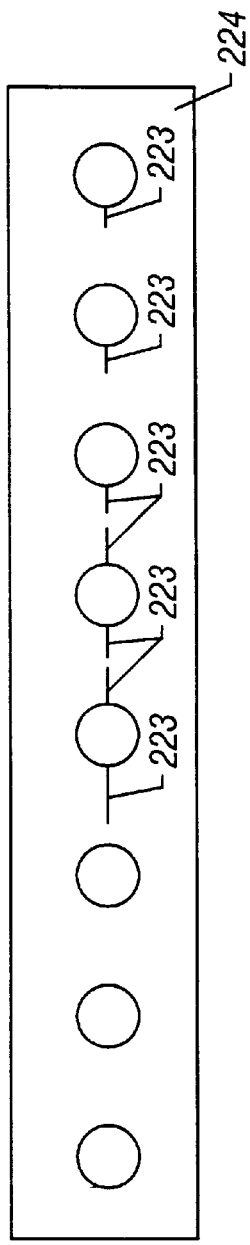

The ability to discriminate fasteners is also shown in FIGS. 11A–D. In FIG. 11A, a cross-sectional view of a two-layer structure 220 having several rivets 222 is shown. The structure 220 is a lapjoint having electrical-discharge-machined (EDM) notches 223 in a bottom layer 224 and rivets 222 on 1-inch centers. The notch 223 lengths and locations are shown in FIG. 11D (a cross-section of the bottom layer 224) to be emanating radially from the edge of the rivet 220 holes. An image display 27 of the scanned structure 220 without time-gating is shown in FIG. 11B, where some of the notches 223 can barely be seen. By contrast, FIG. 11C shows a display 27 after time-gating to eliminate the interference due to the rivets 222, which makes even the smallest notch easy to see.

Calibration

Figure 12:
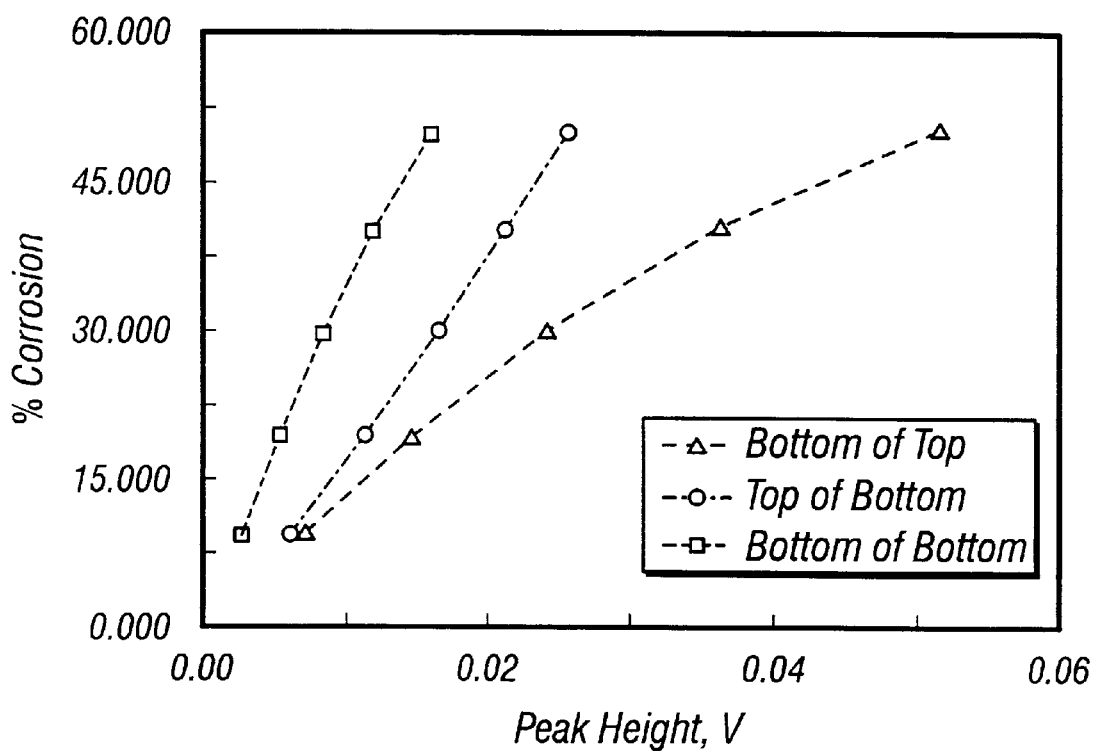
FIG. 12 is a plot of calibration curves of percent corrosion versus difference signal peak amplitude.

The PEC instrument 10 can be calibrated so that it is able to infer the amount of corrosion under a scanned surface. Example calibration curves showing the relationship between the percentage of corrosion (that is, metal thinning) in a particular layer and the corresponding time-domain difference signal peak amplitude (PA) are shown in FIG. 12. The data for the example calibration curves shown in FIG. 12 are taken from the data shown in FIG. 6D. It can be seen from the calibration curves that the amount of corrosion is a function of peak amplitude PA.

The PEC instrument 10 is used to obtain a database of experimental data to construct calibration curves like those shown in FIG. 12. The user takes an initial scan on a calibration sample and a C-scan display of the scanned sample is generated. The user then uses the input device 28 to position the probe 15 at a location of a flaw. The user then presses a "calibrate" button, to enter the following fields for a calibration database file record: (1) the location of the flaw (for example, bottom of top, top of bottom, etc.); (2) the amount of corrosion as a percentage of the total thickness of the layer in which the corrosion appears; (3) mean peak amplitude; and (4) mean zero-axis crossing time. For the first two calibration file fields, the user inputs the relevant data using input device 28. Data for the last two fields are entered automatically after difference signal parameters are acquired for the selected location. Values for the last two of the calibration fields are averaged and the mean computed from several difference signals acquired from that location. The peak amplitude and zero-axis crossing times for the calibration file records, alternatively, can be calculated theoretically. This is done by calculating the reference PEC response signal and the metal-thinned PEC response signal as described above. The difference between the two is then calculated to obtain a theoretical difference signal, from which values for the peak amplitude and the zero-axis crossing time are determined.

Then, to display an image file in a calibration mode, the user first specifies a calibration database file, and also specifies a layer to be displayed (for example, bottom of top, top of bottom, etc.). Selecting the layer establishes a time-gate for filtering, for example, the time-gate can be a range of plus-or-minus 5% of the mean zero-axis crossing times for the calibration samples obtained from the selected layer. Next, data from the calibration database file are read and calibration curves are fit to the data. This is done by performing a least squares regression to a second degree polynomial to obtain an approximate calibration curve. Then, for each image file whose zero-axis crossing time falls within the time-gate, a percentage corrosion value is determined from the peak amplitude by referring to the calibration curve for the specified layer.

A spectrum of five colors are used to color code the amount of corrosion. Each color corresponds to a five percent range of corrosion, for example, the first color represents 0–5% corrosion, the second color 5–10% corrosion, and so forth. These ranges were selected for two reasons. First, the 10% value relates to many manufacturer's specifications which state that where there is more than 10% metal thinning, corrective action must be taken. Second, it was found that if the color ranges were too small (that is, less than 5%), there were problems with noise, and where the ranges were larger, the user was not provided with enough information.

Other Embodiments

Other embodiments are within the scope of the following claims. For example, a time-gate of the time to peak amplitude can be used for filtering, as the time to peak amplitude conveys information similar to that conveyed in the zero-axis crossing time (see FIG. 7). The inventors found, however, that more accurate results are obtainable using zero-axis crossing time, because there is less time separation between different peak amplitude times and also because peak amplitude times are more difficult to pinpoint.

In the PC 100, a discrete Fourier transform can be performed on the digitized time-domain difference signal as it is received from the data acquisition card 140. This gives magnitude values at a spectrum of frequencies, which may number, for example, 256, for the 512 time-domain data points. These magnitude values can be stored in memory 104 with frequency and location information.

Determining and storing the frequency-domain difference signal allows for several possibilities. For example, after a user displays the C-scan image using the time-domain information as was previously described, the user can select, with the input device 28, a point on the image and switch over to a frequency-domain mode to display, at visual display 27, a plot of the stored magnitude values versus frequency for the difference signal acquired from the selected point. This provides additional information to the user about the depth of a detected flaw, and in a frequency-domain format that is conventional for users of eddy current instruments. Another possibility is that the frequency-domain information could be used to create a C-scan image of the inspection results. A frequency, or range of frequencies, can be selected to obtain an image of a particular depth of the inspected structure and to discriminate fasteners and the like. Again, the frequency component corresponds to depth; the lower the frequency, the deeper the depth. The data for any one point of the image display is derived from the magnitude value for frequencies meeting the selected frequency condition.

The principles of the invention can be applied to pulsed eddy current systems that use a probe that acquires a time-domain PEC response in the form of an induced magnetic field, for example, as would be obtained from a Hall sensor, a flux gate sensor, a magnetoresistive sensor, or a superconducting quantum interference device (SQUID). With a time-domain difference signal for a magnetic field PEC response signal, there is no zero-axis crossing time; however, there is a time to peak amplitude that could be used for time-gating.

What is claimed is:

1. A method of displaying information of a structure under inspection with a pulsed eddy current (PEC) instrument, the method comprising:

acquiring a PEC pulse response for a plurality of locations on the structure under inspection;

determining differences between a reference PEC pulse response and each of the acquired pulse responses to obtain a plurality of difference signals;

determining a time value and a magnitude value for each of the difference signals and storing the time values and the magnitude values in memory with location information;

displaying an image of the inspected structure, wherein the display is determined from the stored difference signal magnitude values and location information, and wherein the stored magnitude values for difference signals with stored time values not meeting a defined time condition are filtered from the display.

2. The method of claim 1, wherein the time value is a measure of a zero-axis crossing time following a peak amplitude.

3. The method of claim 1, wherein the time value is a measure of a time to a peak amplitude.

4. The method of claim 1, wherein the magnitude value is a measure of a peak amplitude.

5. The method of claim 1, wherein the plurality of PEC pulse responses are acquired during a scan of the structure under inspection.

6. The method of claim 1, wherein the structure under inspection is a lapjoint of an aircraft.

7. The method of claim 1, further comprising ascertaining the reference PEC pulse response by acquiring a PEC pulse response from a known structure of the type under inspection.

8. The method of claim 1, further comprising ascertaining the reference PEC pulse response theoretically from known geometric characteristics of the structure under inspection.

9. The method of claim 1, further comprising ascertaining the reference PEC pulse response by selecting a PEC response signal database for the type of structure under inspection from a list of PEC response signal databases previously stored in memory.

10. The method of claim 1, wherein the defined time condition is a time-gate.

11. The method of claim 1, wherein the defined time condition is selected by a user.

12. The method of claim 1, further comprising the user selecting a layer to be displayed, wherein the defined time condition is determined from the selected layer to be displayed and information regarding time values expected from that layer.

13. The method of claim 1, wherein the defined time condition comprises a condition of less than or equal to a lower limit, under which the time value for difference signals for known conditions are expected to fall, and over which the time value for difference signals for corrosion conditions in the structure under inspection are expected to fall.

14. The method of claim 13, wherein the lower limit is selected by a user.

15. The method of claim 13, wherein the lower limit is determined from geometric information about the structure under inspection.

16. The method of claim 13, wherein the known conditions comprise the presence of a fastener.

17. The method of claim 13, wherein the known conditions comprise excess lift-off of a probe for the PEC instrument from the inspected structure.

18. The method of claim 13, wherein the known conditions comprise an air gap between layers of the inspected structure.

19. A pulsed eddy current (PEC) inspection apparatus comprising:

a scanning apparatus capable of being positioned over a structure to be inspected;

a PEC probe attached to the scanning apparatus for scanning the probe over the structure during an inspection, wherein the probe supplies step-function excitation to, and senses the PEC response signals from, different locations of the structure;

a processor for determining a difference between a reference PEC response signal and sensed PEC response signals to obtain a difference signal, and for determining a measure of a time value and a magnitude value for the difference signal;

memory for storing the time values, the magnitude values and location information for difference signals; and a visual display device for displaying an image of the inspection results, wherein the image is derived from the stored difference signal magnitude values and location information, and wherein the stored magnitude values for difference signals with stored time values not meeting a defined time condition are filtered from the display.

20. The apparatus of claim 19, wherein the time value is a measure of a zero-axis crossing time following a peak amplitude.

21. The apparatus of claim 20, wherein the magnitude value is a measure of a peak amplitude.

22. The apparatus of claim 19, wherein the time value is a measure of a time to a peak amplitude.

23. The apparatus of claim 19, wherein the defined time condition is a user-selectable time-gate.

24. The apparatus of claim 19, further comprising a layer selector that determines the defined time condition.

25. The apparatus of claim 19, wherein the defined time condition comprises a condition of less than or equal to a lower limit, below which the time value for difference signals for known conditions are known to fall, and above which the time value for difference signals for corrosion conditions in the structure under test are known to fall.

26. The apparatus of claim 25, wherein the lower limit is selected by a user.

27. The apparatus of claim 26, wherein the lower limit is determined from geometric information about the structure under inspection.

28. The apparatus of claim 25, wherein the known conditions comprise the presence of a fastener.

29. The apparatus of claim 25, wherein the known conditions comprise excess lift-off of a probe for the PEC instrument from the inspected structure.

30. The apparatus of claim 25, wherein the known conditions comprise an air gap between layers of the inspected structure.

31. The apparatus of claim 19, wherein the PEC instrument measures the transient current-voltage response function for step-function excitation of a coil.

32. The apparatus of claim 19, wherein the PEC instrument measures the magnetic field response function for step-function excitation of a coil.

33. A method of displaying information for a structure under inspection in a pulsed eddy current (PEC) instrument, the method comprising:

acquiring a PEC pulse response for a location on the structure under inspection;

determining a difference between a reference PEC pulse response and the acquired pulse response to obtain a difference signal;

determining a time value and a magnitude value for the difference signal and storing the time value and the magnitude value in memory;

determining a quantified flaw measure for the inspected location at a specified depth of the inspected structure, by comparing, if the time value meets a time condition associated with the specified depth, the magnitude value to a known calibration curve of magnitude values versus quantified flaw measures.

34. The method of claim 33, further comprising creating the calibration curve by regression analysis of a plurality of acquired difference signal magnitude values taken from a plurality of locations with different known quantified flaw measures at the specified depth.

35. The method of claim 33, further comprising displaying a color-coded representation of the quantified flaw measure.

36. The method of claim 33, further comprising performing the method for plurality of different locations on the structure under inspection, and wherein the color-coded display is an image the inspection results of all of the inspected plurality of locations.

37. The method of claim 33, wherein the magnitude value is a measure of peak amplitude.

38. The method of claim 37, wherein the time value is a measure of a time to zero-axis crossing after the peak amplitude.

39. A method of displaying information of a structure under inspection with a pulsed eddy current (PEC) instrument, the method comprising:

acquiring a PEC pulse response for a location on the structure under inspection;

determining the difference between a reference PEC pulse response and the acquired pulse response to obtain a time-domain difference signal;

performing a Fourier transform on the time-domain difference signal to obtain magnitude values for a plurality of frequencies, and storing the magnitude values in memory in association with the respective frequency;

displaying a plot of the magnitude values versus the plurality of frequencies.

40. A method of displaying information of a structure under inspection with a pulsed eddy current (PEC) instrument, the method comprising:

acquiring a PEC pulse response for a plurality of locations on the structure under inspection;

determining differences between a reference PEC pulse response and the acquired pulse responses to obtain a plurality of time-domain difference signals;

performing Fourier transforms on the time-domain difference signals to obtain, for each difference signal, magnitude values for a plurality of frequencies, and storing the magnitude values in memory in association with the respective frequency and location information;

displaying an image of the inspected structure, wherein the display is determined from the stored magnitude values and location information, and wherein the stored magnitude values associated with a frequency not meeting a defined frequency condition are filtered from the display.

41. The method of claim 40, wherein the defined frequency condition is a frequency-gate.

42. The method of claim 41, wherein the defined frequency condition is selected by a user.

43. The method of claim 40, further comprising the user selecting a layer to be displayed, wherein the defined frequency condition is determined from the selected layer to be displayed and information regarding frequency responses expected from that layer.

44. The method of claim 40, wherein the defined frequency condition comprises a condition of less than or equal to a lower limit that is above a frequency at which known conditions are known to have significant magnitude values.

45. The method of claim 44, wherein the lower limit is determined from geometric information about the structure under inspection.

46. The method of claim 44, wherein the known conditions comprise the presence of a fastener.

47. The method of claim 44, wherein the known conditions comprise excess lift-off of a probe for the PEC instrument from the inspected structure.

48. The method of claim 44, wherein the known conditions comprise an air gap between layers of the inspected structure.

* * * * *